United States Patent [19]

Bakshi

[11] 4,136,112

[45] Jan. 23, 1979

[54] PROCESS FOR PREPARING GLYCOLIC ACID FROM FORMALDEHYDE USING ACETIC ACID

[75] Inventor: Kiran R. Bakshi, El Cerrito, Calif.

[73] Assignee: Chevron Research Company, San Francisco, Calif.

[21] Appl. No.: 809,736

[22] Filed: Jun. 24, 1977

[51] Int. Cl.$^2$ ............................................. C07C 59/06
[52] U.S. Cl. ................................................... 562/518
[58] Field of Search ........................... 260/535, 535 R

[56] References Cited

U.S. PATENT DOCUMENTS

| | | | |
|---|---|---|---|
| 2,153,064 | 4/1939 | Larson | 260/535 R |
| 3,911,003 | 10/1975 | Suzuki | 260/535 R |
| 4,016,208 | 4/1977 | Suzuki | 260/535 R |

*Primary Examiner*—James O. Thomas, Jr.
*Assistant Examiner*—Leah Hendriksen
*Attorney, Agent, or Firm*—D. A. Newell; John Stoner, Jr.; A. T. Bertolli

[57] ABSTRACT

The hydrogen fluoride-catalyzed carbonylation of formaldehyde to prepare glycolic acid can be carried out with a significant reduction in by-product formation and at a significantly improved rate by incorporating minor amounts of acetic acid in the reaction medium.

2 Claims, No Drawings

PROCESS FOR PREPARING GLYCOLIC ACID FROM FORMALDEHYDE USING ACETIC ACID

BACKGROUND OF THE INVENTION

This invention concerns an improved process for preparing glycolic acid by the hydrogen fluoride (HF) catalyzed reaction of formaldehyde and carbon monoxide. In particular, the invention provides a method for reducing by-product formation while increasing the reaction rate by carrying out the reaction in a medium comprising a minor amount of acetic acid.

U.S. Pat. No. 3,911,003, which issued Oct. 7, 1975 to Shigeto Suzuki, describes the HF-catalyzed carbonylation of formaldehyde to glycolic acid. The reaction produces a mixture of glycolic acid and diglycolic acid. However, the yield of glycolic acid can be maximized by carrying out the reaction using aqueous formaldehyde. Where glycolic acid is the desired product, it is especially advantageous to maximize the reaction rate and minimize the formation of by-product.

U.S. Pat. No. 4,016,208, which issued Apr. 5, 1977, to Shigeto Suzuki, describes the carbonylation of formaldehyde using a catalyst comprising HF. Again the reaction produces a mixture of glycolic acid and diglycolic acid. The yield of glycolic acid can be maximized by carrying out the reaction in the presence of added water.

U.S. Pat. No. 3,948,986, which issued on Apr. 6, 1976, to Shigeto Suzuki describes the preparation of an alpha-acyloxy acid by the HF-catalyzed reaction of a $C_2$-$C_{16}$ saturated aldehyde, carbon monoxide, and a $C_1$-$C_6$ saturated carboxylic acid. In Example 5 of this patent, the HF-catalyzed reaction of acetaldehyde, carbon monoxide and acetic acid is illustrated. Acetyl lactic acid was the principal reaction product.

U.S. Pat. No. 3,948,977, which issued on Apr. 6, 1976 to Shigeto Suzuki, describes the preparation of acyloxyacetic acid by the HF-catalyzed reaction of formaldehyde, carbon monoxide and a carboxylic acid. In Example 9, the HF-catalyzed reaction of formaldehyde, carbon monoxide and acetic acid is illustrated. The product contained 86% acetoxyacetic acid.

SUMMARY OF THE INVENTION

It has now been found that when the HF-catalyzed carbonylation of formaldehyde to prepare glycolic acid is carried out in the presence of acetic acid at an acetic acid to formaldehyde mol ratio between about 0.1 and 0.9, the reaction rate is significantly increased and the weight percent of diglycolic acid by-product is significantly reduced.

DETAILED DESCRIPTION OF THE INVENTION

The reaction of formaldehyde with carbon monoxide using a catalyst comprising HF is thoroughly described in U.S. Pat. Nos. 3,911,003 and 4,016,208, which are incorporated herein by reference. The reaction is generally carried out in excess HF. Thus, the HF acts as both the catalyst and reaction medium. In the preferred method, a synthesis gas stream containing hydrogen and carbon monoxide is passed countercurrent to aqueous formaldehyde in the HF medium. The concentration of formaldehyde is about 3 to 35 mol percent, the concentration of water is about 3 to 40 mol percent, and the concentration of HF is about 40 to 90 mol percent.

In accordance with the foregoing patent, reaction temperatures and pressures may vary respectively from about 0° to 100° C and from about 10 to 4000 psig. Further, in accordance with said U.S. Pat. Nos. 3,911,003 and 4,016,208, reaction times varying from 10 minutes to 60 minutes are exemplified.

According to the present process, by adding between about 0.3 and 30 mol percent acetic acid to the reaction medium, the rate of reaction can be nearly doubled and the formation of diglycolic acid essentially eliminated. Expressed as a molar ratio, the amount of acetic acid relative to the amount of formaldehyde which is used to achieve the unexpected results of this invention varies from about 0.1 to about 0.9.

In general, as the mol ratio of acetic acid to formaldehyde is increased, the formation of diglycolic acid is decreased. At an acetic acid to formaldehyde mol ratio of about 0.5, essentially no diglycolic acid is formed. Thus, to reduce the amount of diglycolic acid formed, the preferred mol ratio of acetic acid to formaldehyde is at least about 0.4, preferably from about 0.4 to 0.6.

As the mol ratio of acetic acid to formaldehyde is increased, the rate of reaction also increases until a ratio of about 0.9 is reached. However, it has been found that the rate increase is not constant as the amount of acetic acid increases. In fact, at an acetic acid to formaldehyde mol ratio above about 0.3, the relative rate of reaction begins to decline. Thus, to increase the reaction rate, the preferred molar ratio of acetic acid to formaldehyde is from about 0.1 to 0.4.

Considering both the by-product formation and reaction rate, the preferred mol ratio of acetic acid to formaldehyde is from about 0.3 to 0.5. Especially good results have been obtained at a ratio of about 0.4. At this point, the relative rate of reaction is improved by about 65% and by-product formation is reduced by 60%.

EXAMPLES

The following examples illustrate embodiments of the process provided by this invention and suggest alternative embodiments encompassed by the claims which follow.

In each of the following examples, a 1-liter, stainless steel autoclave with a magnetic stirrer was used as a reactor to carry out carbonylation of formaldehyde. The reactor was charged with 60 grams of trioxane or paraformaldehyde, 18 grams water and 380–400 grams hydrofluoric acid. Acetic acid was added to this mixture in varying amounts (0–120 grams). The autoclave was then placed under 30 psi carbon monoxide (CO) pressure at 120° F, while continuously stirring the contents with the stirrer. The reactor pressure was maintained by continuously feeding CO from a regulated cylinder supply until completion of the reaction. The pressure decrease in the CO cylinder was used to study the rate of carbonylation for various reaction mixtures.

The product obtained from the reactor was analyzed for glycolic acid, acetoxyacetic acid and diglycolic acid by thermal esterification with methanol, followed by gas chromatographic analysis.

The carbonylation rate data are shown in Table I while Table II shows the by-product (diglycolic acid) formation as a function of acetic acid used.

TABLE I

| Ex. No. | Feed Composition (Mols Acetic Acid/Mol Formaldehyde) | Relative Rate of Carbonylation (%) |
|---|---|---|
| 1 | 0 | 100 |
| 2 | 0.26 | 191 |
| 3 | 0.37 | 165 |
| 4 | 0.5 | 123 |
| 5 | 1.0 | 98 |

TABLE II

| Ex. No. | Feed Mol Acetic Acid/Mol Formaldehyde | By-Product Diglycolic Acid (Wt. %) |
|---|---|---|
| 1 | 0 | 7 |
| 2 | 0.26 | 4 |
| 3 | 0.37 | 2.7 |
| 4 | 0.5 | undetectable |
| 5 | 1.0 | undetectable |

What is claimed is:

1. In a process for preparing glycolic acid by the hydrogen fluoride-catalyzed reaction of formaldehyde and carbon monoxide, the improvement which comprises carrying out the reaction in the presence of acetic acid in an amount of at least 0.3 mol for each mol of formaldehyde but less than 0.5 mol of acetic acid for each mol of formaldehyde.

2. In a process for preparing glycolic acid by contacting a synthesis gas comprising carbon monoxide and hydrogen with aqueous formaldehyde in a hydrogen fluoride reaction medium, the improvement which comprises effecting said contacting in a reaction medium comprising hydrogen fluoride and in addition thereto acetic acid, the acetic acid being present in an amount of at least about 0.3 mol for each mol of formaldehyde but less than 0.5 mol of acetic acid for each mol of formaldehyde.